US006753407B2

(12) United States Patent
Noga et al.

(10) Patent No.: US 6,753,407 B2
(45) Date of Patent: Jun. 22, 2004

(54) ANTIMICROBIAL PEPTIDES ISOLATED FROM FISH

(75) Inventors: Edward J. Noga, Raleigh, NC (US); Umaporn Silphaduang, Fuquay-Varina, NC (US)

(73) Assignee: North Carolina State University, Raleigh, NC (US)

(*) Notice: Subject to any disclaimer, the term of this patent is extended or adjusted under 35 U.S.C. 154(b) by 0 days.

(21) Appl. No.: 09/929,788

(22) Filed: Aug. 14, 2001

(65) Prior Publication Data

US 2003/0083247 A1 May 1, 2003

Related U.S. Application Data

(60) Provisional application No. 60/225,354, filed on Aug. 15, 2000.

(51) Int. Cl.$^7$ .................................................. A61K 38/00

(52) U.S. Cl. .................... 530/326; 530/300; 424/184.1; 424/184.5; 514/2; 514/13; 514/21

(58) Field of Search ................................ 530/300, 326; 424/184.1, 185.1; 514/2, 13, 21

(56) References Cited

FOREIGN PATENT DOCUMENTS

| | | |
|---|---|---|
| WO | WO 89/00199 | 1/1989 |
| WO | WO 94/21672 | 9/1994 |

OTHER PUBLICATIONS

Robinette, D., et al., *Antimicrobial activity in the skin of the channel catfish Ictalurus punctatus: characterization of broad–spectrum histone–like antimicrobial proteins, CMLS Cellular and Molecular Life Sciences*, vol. 54, pp. 467–475 (1998).

Yu, K., et al., *Relationship between the tertiary structures of mastoparan B and its analogs and their lytic activities studied by NMR spectroscopy, J. Peptide Res.*, vol. 55, pp. 51–62 (2000).

Boman, Hans, *Peptide Antibiotics and Their Role in Innate Immunity, Annual Review of Immunology*, vol. 13, pp. 61–92 (1995).

Silphaduang, et al., *Peptide Antibiotics in Mast Cell of Fish, Nature*, vol. 414, No. 6861, pp. 268–269 (Nov. 15, 2001).

*Primary Examiner*—Lynette R. F. Smith
*Assistant Examiner*—Robert A. Zeman
(74) *Attorney, Agent, or Firm*—Myers Bigel Sibley & Sajovec

(57) ABSTRACT

Antimicrobial peptides (endobiotic peptides), isolated from fish are described. Such endobiotic peptides may be isolated as 22 amino acid peptides having molecular weights of about 2500 Da from the gills of hybrid striped bass (*Morone saxitilis*×*Morone chrysops*). Antibodies that bind such peptides and methods of using such peptides are also described.

2 Claims, No Drawings

```
                         SEQUENCE LISTING


<160> NUMBER OF SEQ ID NOS: 5

<210> SEQ ID NO 1
<211> LENGTH: 22
<212> TYPE: PRT
<213> ORGANISM: Morone saxitilis x Morone chrysops

<400> SEQUENCE: 1

Phe Ile His His Ile Phe Arg Gly Ile Val His Ala Gly Arg Ser Ile
1               5                   10                  15

Gly Arg Phe Leu Thr Gly
            20
```

-continued

```
<210> SEQ ID NO 2
<211> LENGTH: 22
<212> TYPE: PRT
<213> ORGANISM: Morone saxitilis x Morone chrysops

<400> SEQUENCE: 2

Phe Phe His His Ile Phe Arg Gly Ile Val His Val Gly Lys Thr Ile
1               5                   10                  15

His Arg Leu Val Thr Gly
            20


<210> SEQ ID NO 3
<211> LENGTH: 22
<212> TYPE: PRT
<213> ORGANISM: Morone saxitilis x Morone chrysops

<400> SEQUENCE: 3

Phe Phe His His Ile Phe Arg Gly Ile Val His Val Gly Lys Thr Ile
1               5                   10                  15

His Lys Leu Val Thr Gly
            20


<210> SEQ ID NO 4
<211> LENGTH: 44
<212> TYPE: PRT
<213> ORGANISM: Morone saxitilis x Morone chrysops
<220> FEATURE:
<221> NAME/KEY: MISC_FEATURE
<222> LOCATION: (20)..(20)
<223> OTHER INFORMATION: "X" is unknown

<400> SEQUENCE: 4

Phe Phe Arg His Leu Phe Arg Gly Ala Lys Ala Ile Phe Arg Gly Ala
1               5                   10                  15

Arg Gln Gly Xaa Arg Ala His Lys Val Val Ser Arg Tyr Arg Asn Arg
            20                  25                  30

Asp Val Pro Glu Thr Asp Asn Asn Gln Glu Glu Pro
        35                  40


<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

His Ile Phe Arg
1
```

ANTIMICROBIAL PEPTIDES ISOLATED FROM FISH

RELATED APPLICATIONS

This application claims the benefit of U.S. Provisional Application Serial No. 60/225,354, filed Aug. 15, 2000, the disclosure of which is incorporated by reference herein in its entirety.

GOVERNMENT SUPPORT

This invention was made with Government support under University of North Carolina Sea Grant NA86-RG-0036 and United States Department of Commerce Grant NA90AA-DSG-062. The Government has certain rights to this invention.

FIELD OF THE INVENTION

The present invention relates to two families of novel antimicrobial peptides exhibiting therapeutic antimicrobial properties, to antibodies that specifically bind to one of the families of the novel peptides, and to methods of monitoring and improving health in aquaculture species and of preservation of seafood.

BACKGROUND OF THE INVENTION

Infectious diseases are often the most serious impediment to the success of the commercial aquaculture industry in the United States and worldwide. The epithelial surfaces of fish, such as the skin, gills and alimentary tract, provide first contact with potential pathogens. It has been reported that several kinds of endogenous antimicrobial peptides exist in the skin, stomach and blood of amphibians, mammals and insects. Examples include cecropins (insects), defensins (mammals, insects), and magainins (frogs) (See discussion infra, Detailed Description of Preferred Embodiments). These peptides exhibit antimicrobial activity against a broad spectrum of organisms. This ability to exhibit broad-spectrum activity provides the advantages of nonspecificity and rapid response. These advantages enable the host to delay or prevent microbial colonization. Enhancement of nonspecific defenses exhibiting a broad range of activity against numerous pathogens may be a cost-effective method of controlling disease epidemics that inhibit successful aquacultural endeavors.

Therefore, it is an objective of this invention to provide a better understanding of the mechanisms responsible for disease resistance in aquatic animals and to use this knowledge to reduce epidemic disease. Additionally, this invention may aid in the development of peptide antibiotics for the treatment of human diseases. Other features and advantages of the present invention will be more apparent in the detailed description set forth below.

SUMMARY OF THE INVENTION

A first aspect of the present invention is an antimicrobial compound or endobiotic peptide isolated from fish. The compound may be selected from the group consisting of peptides having an amino acid sequence selected from the group consisting of: SEQ ID NO: 1; SEQ ID NO: 2; SEQ ID NO: 3, or SEQ ID NO: 4.

A further aspect of the present invention is a pharmaceutical formulation comprising a compound as described above in a pharmaceutically acceptable carrier.

A further aspect of the present invention is an antibody (e.g., a monoclonal antibody) that specifically binds to a compound as described above.

A further aspect of the invention is a method of treating stress in fish, comprising administering an endobiotic peptide as described above to a fish in an amount effective to treat or combat stress therein.

A further aspect of the invention is a nucleic acid (e.g., a DNA) that encodes a peptide as described above.

A further aspect of the invention is a method of treating stress in fish, comprising administering a nucleic acid to the fish (e.g., by injecting the nucleic acid into muscle of the fish) in an amount effective to treat or combat stress therein.

A further aspect of the invention is a method of monitoring fish health, comprising the steps of: (a) collecting a biological sample from a fish; and (b) detecting the level of at least one endogenous endobiotic peptide in the sample, wherein lower levels of endobiotic peptides indicate decreased health in the fish. Examples of suitable endobiotic peptides include, but are not limited to, the peptides described above.

A further aspect of the invention is a method of monitoring freshness of a fish food product, the method comprising detecting the level of at least one endogenous endobiotic peptide, wherein lower levels of endobiotic peptides indicate decreased freshness in the fish food product. Examples of suitable endobiotic peptides include, but are not limited to, the peptides described above.

A further aspect of the present invention is a method of screening for compounds useful for treating stress in fish, the method comprising the steps of: (a) administering a test compound to a fish; (b) collecting a biological sample from the fish; and (c) detecting the level of at least one endogenous endobiotic peptide in the sample, wherein higher levels of endobiotic peptide in the fish as compared to those found in the absence of administration of the test compound indicate the compound is useful in treating stress in the fish. Examples of suitable endobiotic peptides include, but are not limited to, the peptides described above.

DETAILED DESCRIPTION OF THE PREFERRED EMBODIMENT

The present invention will now be described more fully hereinafter with reference to the accompanying figures, in which preferred embodiments of the invention are shown. This invention may, however, be embodied in different forms and should not be construed as limited to the embodiments set forth herein. Rather these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which the invention belongs. All publications, patent applications, patents, and other references mentioned herein are incorporated by reference in their entirety.

Amino acid sequences disclosed herein are presented in the amino to carboxy direction, from left to right. The amino and carboxy groups are not presented in the sequence. Amino acids are represented herein in by single letter code.

"Amino acid sequence" as used herein, refers to an oligopeptide, peptide, polypeptide, or protein sequence, and fragment thereof, and to naturally occurring or synthetic molecules. Where "amino acid sequence" is recited herein to refer to an amino acid sequence of a naturally occurring protein molecule, amino acid sequence, and like terms, are not meant to limit amino acid sequence to the complete, native amino acid sequence associated with the recited protein molecule.

As used herein, the term "antibody" refers to all types of immunoglobulins, including IgG, IgM, IgA, IgD, and IgE. Of these IgM and IgG are particularly preferred. The antibodies may be monoclonal or polyclonal and may be of any species of origin including (for example) mouse, rat, rabbit, horse, or human, or may be chimeric antibodies. See, e.g., M. Walker et al., *Molec. Immunol.* 26, 403–11 (1989). Antibodies that bind to the peptides of Endobiotic Family 1 and/or Endobiotic Family 2 can be prepared using intact peptides or fragments containing small peptides of interest as the immunizing antigen. The peptide or oligopeptide used to immunize an animal can be derived from the translation of RNA or synthesized chemically and can be conjugated to a carrier protein, if desired. Commonly used carriers that are chemically coupled to peptides include bovine serum albumin, thyroglobulin, and keyhole limpet hemocyanin. The coupled peptide is then used to immunize the animal (e.g., a mouse, a rat, or a rabbit).

The term "antimicrobial", as used herein, refers to the ability to terminate or inhibit the growth of microorganisms.

The term "biological sample", as used herein, is used in its broadest sense. A biological sample of a fish may include blood, urine, muscle tissue, skin, gills, viscera, mucosal swab, cell culture, or an aqueous medium housing the fish.

As used herein, the term "endobiotic", refers to a naturally-occurring, host-produced antibiotic. The vast majority of these endogenous antibiotics are low molecular weight peptides or proteins that exhibit antimicrobial activity against a wide range of microorganisms, including bacteria, viruses, fungi, metazoan and protozoan parasites (Robinette et. al., (1998) *Cell. Mol. Life Sci.* 54, 467–475). Examples of endobiotics include cecropins (Bowman, H. (1995) *Ann. Rev. Immunol.* 13: 61–92; Steiner et al., (1981) *Nature* 292: 246–248), defensins (Selsted et al., *J. Biol. Chem.* 258: 14485–14489; Lehrer et al. *Ann. Rev. Immunol.* 11: 105–128), and magainins (Zasloff, M. (1987) *Proc. Natl. Acad. Sci.* USA 84: 5449–5453). Endobiotics reported and characterized in fish include lysozyme (Roberts, R. (1989) *Fish Pathology,* $2^{nd}$ ed., Bailliere Tindall, London), the aminosterol antibiotic squalamine (Moore et al., (1993) *Proc. Natl. Acad. Sci. USA* 90: 1354–1358), and histone-like proteins (Robinette et al., (1998) *Cell. Mol. Life Sci.* 54, 467–475). Other examples include parasin from catfish (Park et al., *FEBS Letters* 437, 258–262 (1998), migurin from Loach (Park et al., *FEBS Letters* 411, 173–178 (1997)), pleurocidin from founder (Cole et al., *Journal of Biological Chemistry* 272, 12008–12013 (1997)), and a <3 Da peptide from rainbow trout. (V. Smith et al., *Fish & shellfish Immunology* 10, 243–260 (2000)).

"Fish", as used herein, refers to any species of fish susceptible to infectious diseases, particularly bony fishes belonging to the class Osteichthyes, and more particularly its subclass Actinopterygii. Such examples include hybrid striped bass, *Morone saxitilis*×*Morone chrysops*, channel catfish, *Ictalurus punctatus*, members of the family salmonidae, including members of the genus Oncorhynchus and salmo such as rainbow trout, *Oncorhynchus mykiss*, flounders (Pleuronectidae and related familes, (carps (family cyprinidae), sturgeons (family acipenseridae), sunfish (family centrarchidae), mullets (family muglidae), milkfish (*Chanos chanos*), yellow perch (family percidae), tilapia (family Cichlidae), etc.

"Fish health", as used herein, refers to the physiological and behavioral responses of fish to stress. Stress is a major predisposing factor for infectious disease in fish (Meyer, F (1970) Seasonal Fluctuations in the Incidence of Disease on Fish Farms. In: Snieszko, S (ed) A Symposium on Diseases of fishes and shellfishes. Special Publication no 5, American Fisheries Society, Washington, D.C.; Walters, G and Plumb, J (1980) *J. Fish Biol.* 17: 177–185; Barton (1997) Stress in Finfish: Past, Present, and Future—A Historical Perspective. In: Iwana et al. (eds) Fish Stress and Health in Aquaculture. *Soc. Exper. Biol. Seminar Series* 62: 1–34, Cambridge University Press, New York). A number of stressors commonly associated with aquaculture can adversely impact or impair the fish immune system, including crowding (Klinger et al. (1983) *Aquaculture* 30: 263–272), handling (Ellsaesser, D and Clem, L. (1986) *J. Fish Biol.* 28: 511–521), temperature fluctuation (Clem et al. (1984) *Dev. Comp. Immunol.* 8: 313–322; Miller, N. and Clem, L. (1984) *J. Immunol.* 133: 2356–2359) and poor water quality (Smart, G (1981) Aspects of Water Quality Producing Stress in Intensive Fish Culture. In Pickering, A (ed) Stress and Fish, Academic Press, London, p 277–294; Schwedler et al. (1985) Non-infectious Diseases. In: Tucker, C (ed) Channel Catfish Culture. Developments in Aquaculture and Fisheries Science. Vol 15, Elsevier, Amsterdam, p 497–541). Fish health also includes the immune response of the fish. Thus, the terms treating or combating stress as used herein include enhancing or improving fish immune function that has been impaired, or will be impaired, by a stressor.

"Freshness", as used herein, is used in its broadest sense and refers to the absence of spoilage in a human food product.

This invention also encompasses the nucleic acid molecules that encode the peptides described herein. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., TETRAHEDRON, 49 (10): 1925 (1993) and references therein; Letsinger, *J. Org. Chem.,* 35: 3800 (1970); Sprinzl, et al., *Eur. J. Biochem.,* 81: 579 (1977); Letsinger, et al., *Chemica Scripta,* 26: 141 (1986)), phosphorothioate (Mag, et al, *Nucleic Acids Res.,* 19: 1437 (1991); and U.S. Pat. No. 5,644,048), phosphorodithioate (Briu, et al., *J. Am. Chem. Soc.,* 111: 2321 (1989)), O-methylphosphoroamidite linkages (see Eckstein, Oligonucleotides and Analogues: A Practical Approach, Oxford University Press), and peptide nucleic acid backbones and linkages (see Egholm, *J. Am. Chem. Soc.,* 114: 1895 (1992); Meier, et al., *Chem. Int. Ed. Engl.,* 31: 1008 (1992); Nielsen, *Nature,* 365: 566 (1993); Carlsson, et al., *Nature,* 380: 207 (1996), all of which are incorporated by reference)). Other analog nucleic acids include those with positive backbones (Denpcy, et al., *Proc. Natl. Acad. Sci. USA,* 92: 6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English,* 30: 423 (1991); Letsinger, et al., *J. Am. Chem. Soc.,* 110: 4470 (1988); Letsinger, et al., NUCLEOSIDE & NUCLEOTIDE 13: 1597 (1994); Chapters 2 and 3, ASC Symposium Series 580, "Carbohydrate Modifications in Antisense Research," Ed. Y. S. Sanghui and P. Dan Cook; Mesmaeker, et al., *Bioorganic & Medicinal Chem. Lett.,* 4: 395 (1994); Jeffs, et al, *J. Biomolecular NMR,* 34: 17 (1994); Tetrahedron Lett (CAPITALIZE)., 37: 743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research," Ed. Y. S. Sanghui and P. Dan Cook. Nucleic acids containing one or more carbocyclic sugars are also included within the definition of nucleic acids (see Jenkins, et al., *Chem. Soc. Rev.*, (1995) pp. 169–176). Several nucleic acid analogs are described in Rawls, *C & E News*, Jun. 2, 1997, page 35. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acids analogs, and mixtures of naturally occurring nucleic acids and analogs may be made. The nucleic acids may be single stranded or double stranded, as specified, or contain portions of both double stranded or single stranded sequence. The nucleic acid contains any combination of deoxyribo-and ribo-nucleotides, and any combination of bases, including uracil, adenine, thymine, cytosine, guanine, inosine, xathanine, hypoxathanine, isocytosine, isoguanine, etc.

As used herein, the term "peptide" refers to an oligomer of at least two contiguous amino acid residues.

The term "pharmaceutically acceptable" as used herein means that the compound or composition is suitable for administration to a subject to achieve the treatments described herein, without unduly deleterious side effects in light of the severity of the disease and necessity of the treatment.

A. Peptide Production and Pharmaceutical Formulations

The methods for making peptides entail, unless otherwise noted, conventional techniques of synthetic organic chemistry, protein chemistry, molecular biology, microbiology, and recombinant DNA technology, which are within the skill of one in the art. Such techniques are fully explained in the literature. See, e.g., Scopes (1987), *Protein Purification Principles and Practice,* 2d Ed, Springer-Verlag; *Methods in Enzymology*, Colowick and Kaplan, eds., Academic Press, Inc.; Sambrook et al., (1989) *Molecular Cloning: A Laboratory Manual* (2d Ed. 1989) (Cold Spring Harbor, N.Y.); *Handbook of Experimental Immunology*, (1986) Vols. I–V, Weir and Blackwell, eds, Blackwell Scientific Publications; House (1972), *Modern Synthetic Reactions,* 2d ed., Benjamin/Cummings, Menlo Park, Calif.; Arherton and Sheppard (1989), *Solid Phase Peptide Synthesis: A Practical Approach*, Oxford University Press; Steward and Young, *Solid Phase Peptide Synthesis* (1984), 2d Ed., Pierce Chemical Co.

The peptides of the present invention may be extended at either the N-terminus or the C-terminus or both termini by the addition of 1 to 10 amino acids, preferably 1 to 5, and more preferably 4.

Pharmaceutical formulations of the present invention comprise compounds with pharmacological activity (as identified using methods of the present invention) in a pharmaceutically acceptable carrier. Suitable pharmaceutical formulations include those suitable for inhalation, oral, rectal, topical, (including buccal, sublingual, dermal, vaginal and intraocular), parenteral (including subcutaneous, intradermal, intramuscular, intravenous, intraperitoneal, and intraarticular) and transdermal administration. The compositions may conveniently be presented in unit dosage form and may be prepared by any of the methods well known in the art. The most suitable route of administration in any given case may depend upon the anatomic location of the condition being treated in the subject, the nature and severity of the condition being treated, and the particular pharmacologically active compound which is being used. The formulations may conveniently be presented in unit dosage form and may be prepared by any of the methods well known in the art.

In the manufacture of a medicament according to the invention (the "formulation"), pharmacologically active compounds or the physiologically acceptable salts thereof (the "active compounds") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 99% by weight of the active compound. One or more active compounds may be incorporated in the formulations of the invention, which formulations may be prepared by any of the well known techniques of pharmacy consisting essentially of admixing the components, optionally including one or more accessory therapeutic ingredients.

The therapeutically effective dosage of any specific pharmacologically active compound identified by methods on the invention, the use of which compounds is in the scope of the present invention, will vary somewhat from compound to compound, and subject to subject, and will depend upon the condition of the patient and the route of delivery.

Applications for the novel antimicrobial peptides of the present invention may include treating stress in fish and monitoring fish health. Various stresses cause a decrease in endobiotic levels before the fish show any signs of disease. (Compare Noga, E. J., D. P. Engel, T. W. Arroll, S. McKenna and M. Davidian. 1994. Low serum antibacterial activity coincides with increased prevalence of shell disease in blue crabs, *Callinectes sapidus*. Diseases of Aquatic Organisms 19:121–128).

Thus, measurement of these novel endobiotic peptides may provide an indication of chronic and/or acute stress in fish as well as provide an early indication of potential health problems in fish. The inverse relationship between endobiotic levels and stress also provides the basis for assessment of freshness of a fish food product.

Also, these novel peptides may act as cytokines. There is evidence that the cell type containing the 2500 Da peptide of the present invention is the mast cell. Mast cells are known to attract other types of immune cells during inflammatory events in mammals, and there is also evidence for this mechanism in fish. Therefore, the peptides of the present invention are involved in this chemoattraction. Currently, a number of cytokines are being examined as human therapeutic agents in various diseases including cancer.

Additionally, the novel endobiotic peptides of the present invention may also possess neuroactive function. It is highly likely that these novel peptides interact with target membranes in their interaction with microbes. This interaction most likely involves channel formation. Note that another peptide antibiotic isolated from flunder has both antibacterial and neurological activity (Oren Z and Y Shai. 1996. A class of highly potent antibacterial peptides derived from pardaxin, a pore-forming peptide from the Moses sole fish *Pardachirus marmoratus. Eur. J. Biochem.* 237:304–310).

B. Peptide Analogs

An "analog" is a chemical compound similar in structure to a first compound, and having either a similar or opposite physiologic action as the first compound.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. patent references cited herein be incorporated by reference herein in their entirety). See also Waldrop, *Science* 247, 28029 (1990); Rossmann, *Nature* 333, 392 (1988); Weis et al., *Nature* 333, 426 (1988); James et al., *Science* 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

Analogs may also be developed by generating a library of molecules, selecting for those molecules which act as ligands for a specified target, and identifying and amplifying the selected ligands. See, e.g., Kohl et al., *Science* 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, Feb. 7, 1994) and nonpeptide polymers (see, e.g., "peptoids" of Simon et al., *Proc. Natl. Acad. Sci. USA* 89, 9367 (1992)). See also U.S. Pat. No. 5,270,170 to Schatz; Scott and Smith, *Science* 249, 386–390 (1990); Devlin et al., *Science* 249, 404–406 (1990); Edgington, *BIO/Technology* 11, 285 (1993). Peptide libraries may be synthesized on solid supports, or expressed on the surface of bacteriophage viruses (phage display libraries). Techniques are known in the art for screening synthesized molecules to select those with the desired activity, and for labeling the members of the library so that selected active molecules may be identified. See, e.g., Brenner and Lerner, *Proc. Natl. Acad. Sci. USA* 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of viral transcription); Simon et al., *Proc. Natl. Acad. Sci. USA* 89, 9367 (1992) (generation and screening of "peptoids", oligomeric N-substituted glycines, to identify ligands for biological receptors); U.S. Pat. No. 5,283,173 to Fields et al., (use of genetically altered *Saccharomyces cerevisiae* to screen peptides for interactions).

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

C. Antibodies

Antibodies that specifically bind to the peptides of the present invention (i.e., antibodies which bind to a single antigenic site or epitope on the peptides) are useful for a variety of diagnostic purposes.

Antibodies to SEQ ID NO: 1, SEQ ID NO: 2, and/or SEQ ID NO 3 may be generated using methods that are well known in the art. Such antibodies may include, but are not limited to, polyclonal, monoclonal, chimeric, single chain, Fab fragments, and fragments produced by a Fab expression library.

For the production of antibodies, various hosts including goats, rabbits, rats, mice, humans, and others, may be immunized by injection with the endobiotic peptides or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to the endobiotic peptides have an amino acid sequence consisting of at least five amino acids and more preferably at least 10 amino acids.

Monoclonal antibodies to the endobiotic peptides may be prepared using any technique which provides for the production of antibody molecules by continuous cell lines in culture. These include, but are not limited to, the hybridoma technique, the human B-cell hybridoma technique, and the EBV-hybridoma technique. See, e.g., Kohler, G. et al. (1975) *Nature,* 256: 495–497; Kozbor et al. (1985) *J. Immunol. Methods* 81: 31–42; Cote et al. (1983) *Proc. Natl. Acad. Sci. USA* 80: 2026–2030; Cole et al. (1984) *Mol. Cell Biol.* 62: 109–120.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the endobiotic peptide and its specific antibody. A two-site, monoclonal-based immunoassay utilizing monoclonal antibodies reactive to two non-interfering endobiotic peptide epitopes is preferred, but a competitive binding assay may also be employed.

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g. $^{35}S$, $^{125}I$, $^{131}I$), enzyme labels (e.g., horseradish peroxidase, alkaline phosphatase), and fluorescent labels (e.g., fluorescein) in accordance with known techniques.

Kits for determining if a sample contains proteins of the present invention will include at least one reagent specific for detecting the presence or absence of the protein. Diagnostic kits for carrying out antibody assays may be produced in a number of ways. In one embodiment, the diagnostic kit comprises (a) an antibody which binds proteins of the present invention conjugated to a solid support and (b) a second antibody which binds peptides of the present invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed out instructions for carrying out the test.

D. Nucleic Acid Production and Administration

This invention also encompasses the nucleic acid molecules that encode the peptides described herein. Methods of nucleic acid production are well known to those skilled in the art, and the nucleic acids of the present invention are formulated essentially in the manner previously described for peptide production. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron,* 49 (10): 1925 (1993) and references therein; Letsinger, *J. Org. Chem.,* 35: 3800 (1970); Sprinzl, et al., *Eur. J. Biochem.,* 81: 579 (1977); Letsinger, et al., *Chemica Scripta,* 26: 141 (1986)), phosphorothioate (Mag, et al., *Nucleic Acids Res.,* 19: 1437 (1991); and U.S. Pat. No. 5, 644, 048), phosphorodithioate (Briu, et al., *J. Am. Chem. Soc.,* 111: 2321 (1989)), O-methylphosphoroamidite linkages (see Eckstein, Oligonucleotides and Analogues: A Practical Approach, Oxford University Press), and peptide nucleic acid backbones and linkages (see Egholm, *J. Am. Chem. Soc.,* 114: 1895 (1992); Meier, et al., *Chem. Int. Ed. Engl.,* 31: 1008 (1992); Nielsen, *Nature,* 365: 566 (1993); Carlsson, et al., *Nature,* 380: 207 (1996), all of which are incorporated by reference)). Other analog nucleic acids include those with positive backbones (Denpcy, et al., *Proc. Natl. Acad. Sci. USA,* 92: 6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English,* 30: 423 (1991); Letsinger, et al., *J. Am. Chem. Soc.,* 110: 4470 (1988); Letsinger, et al., *Nucleoside & Nucleotide* 13: 1597 (1994); Chapters 2 and 3, ASC Symposium Series 580, "Carbohydrate Modifications in Antisense Research," Ed. Y. S. Sanghui and P. Dan Cook; Mesmaeker, et al., *Bioorganic & Medicinal Chem. Lett.,* 4: 395 (1994); Jeffs, et al, *J. Biomolecular NMR,* 34: 17 (1994); *Tetrahedron Lett,* 37: 743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research," Ed. Y. S. Sanghui and P. Dan Cook. Nucleic acids containing one or more carbocyclic sugars are also included within the definition of nucleic acids (see Jenkins, et al., *Chem. Soc. Rev.*, (1995) pp. 169–176). Several nucleic acid analogs are described in Rawls, *C & E News*, Jun. 2, 1997, page 35. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acids analogs, and mixtures of naturally occurring nucleic acids and analogs may be made. The nucleic acids may be single stranded or double stranded, as specified, or contain portions of both double stranded or single stranded sequence. The nucleic acid contains any combination of deoxyribo-and ribo-nucleotides, and any combination of bases, including uracil, adenine, thymine, cytosine, guanine, inosine, xathanine, hypoxathanine, isocytosine, isoguanine, etc.

Administration of the nucleic acids of the present invention may be administered according to the methods disclosed in Felgner et al. U.S. Pat. No. 5,580,859, or Wolff et al., U.S. Pat. No. 5,693,622 (applicants specifically intend that the disclosures of all U.S. patent references cited herein be incorporated by reference herein in their entirety). Polynucleotide sequences comprising DNA or RNA molecules that are free from any delivery vehicle that acts to facilitate entry into the cell, can be directly administered by injection into tissues. These naked polynucleotide sequences lead to the expression of the endobiotic peptides of the present invention within the subject thereby exerting a pharmacological effect.

The following Examples are provided to illustrate the present invention, and should not be construed as limiting thereof.

EXAMPLE 1

Isolation of Antimicrobial Peptides from Hybrid Striped Bass

At least two families of antimicrobial peptides which have no known sequence homology to any other polypeptides in the NCBI nr or est databases have been isolated from the gills of hybrid striped bass (*Morone saxitilis*×*Morone chrysops*). Endobiotic Family 1 currently consists of 3 peptides, all 22 amino acids long, with a highly homologous N-terminus stretch. These peptides have a molecular weight of about 2500 Da. Endobiotic Family 2 currently consists of 1 peptide at least 44 amino acids long, with the first 6 of 8 amino acids at the N-terminus homologous to those in Endobiotic Family 1. This peptide currently has a molecular weight of about 5329 Da.

EXAMPLE 2

Determination of Molecular Weight and Amino Acid Sequence

The molecular weight of the antimicrobial peptides purified in Example 1 from Endobiotic Family 1 was determined as 2490 Da, 2570 Da, and 2542 Da by the aid of mass spectroscopy. Further amino acid sequence analysis of these three peptides revealed that they are novel peptides consisting of 22 amino acids represented as:

```
FIHHIFRGIVHAGRSIGRFLTG        [SEQ ID NO:1]
FFHHIFRGIVHVGKTIHRLVTG        [SEQ ID NO:2]
FFHHIFRGIVHVGKTIHKLVTG        [SEQ ID NO:3]
```

The molecular weight of the antimicrobial peptide purified in Example 1 from Endobiotic Family 2 was determined as 5329 Da by the aid of mass spectroscopy. Further amino acid sequence analysis of this peptide revealed that it is a novel peptide consisting of a partial amino acid sequence represented as:

FFRHLFRGAKAIFRGARQGXRAHKVVS-RYRNRDVPETDNNQ (E)(E)(P) [SEQ ID NO: 4]
( )=tentative
X=UNKNOWN, POSSIBLY MODIFIED

EXAMPLE 3

Measurement of Antimicrobial Activity of the Peptides

The antimicrobial activity of the peptides in Endobiotic Family 1 was measured by assessing its antibacterial activity against *Escherichia coli* (*E. coli*). The potency of these peptides against *E. coli* is comparable to that exhibited by some of the strongest naturally-occurring antibacterial peptides (e.g., maganins). More specifically, the N-terminal fragment of Endobiotic Family 1 exhibits strong antibacterial activity, and a 10 amino acid section is believed to be primarily responsible for the activity.

EXAMPLE 4

Production of Antibodies to the Peptides

A peptide antibody against Endobiotic Family 1 was produced. The peptide HIFR [SEQ ID NO: 5] (also corresponding to amino acid positions 1 to 11 of SEQ ID NO: 2 and SEQ ID NO: 3) was chemically conjugated to KLH as a carrier. The preparation was injected into rabbits. Serum from the rabbits was processed over an affinity column having the peptide fragment linked to the to capture antibodies specific for the peptide.

EXAMPLE 5

Histone-Like Antimicrobial Protein in Channel Catfish

A partial N-terminal amino acid sequence of a predominate antimicrobial protein found in the skin of channel catfish (*Ictalurus punctatus*) exhibits approximately 89% homology with rainbow trout (*Salmo trutta*) histone H2B, and thus was designated histone-like protein (HLP) (Robinette et. al., (1998) *Cell. Mol. Life Sci.* 54, 467–475). HLPs are broad-spectrum antimicrobial polypeptides that appear to be an important component of nonspecific immunity in the skin of channel catfish (Robinette et. al., (1998) *Cell. Mol. Life Sci.* 54, 467–475).

Healthy, unstressed fish exhibit consistently high levels of a predominate HLP (HLP-1) when measured using ELISA. Fish exposed to chronic stress consisting of overcrowding and elevated ammonia for 1 week showed significantly depressed levels of HLP-1, and fish exposed to stress for 3 or 4 weeks exhibited further depressed levels of HLP-1 (Robinette, D. W. and Noga, E. J., Unpublished Data). The time-dependent decrease in HLP-1 levels was not accompanied by any gross signs of disease (Robinette, D. W. and Noga, E. J., Unpublished Data). The suppression of HLP-1 in the absence of clinical signs of disease along with evidence that HLP-1 levels are not affected by acute stresses of capture or sampling, suggests that HLP levels may be a promising indicator for monitoring fish health.

EXAMPLE 6

Summation of Experimental Results

Two lines of evidence provided herein demonstrate that Endobiotic Family 1 and Endobiotic Family 2 represent a novel family of antimicrobial peptides. First, thus far, these families have no known sequence homology to any other polypeptides in the NCBI nr or est databases. Second, the peptides of Endobiotic Family 1 exhibit potency against *E. coli* that is comparable to that exhibited by some of the strongest naturally occurring antibacterial peptides. Additionally, the N-terminal fragment of the peptides of Endobiotic Family 1 exhibit strong antibacterial activity, and a 10 amino acid section may be primarily responsible for the activity.

The foregoing examples are illustrative of the present invention, and are not to be construed as limiting thereof. The invention is described by the following claims, with equivalents of the claims to be included therein.

---

That which is claimed is:

1. An antimicrobial peptide having an amino acid sequence selected from the group consisting of:

SEQ ID NO: 1;

SEQ ID NO: 2; and

SEQ ID NO: 3.

2. A pharmaceutical formulation comprising a peptide according to claim 1 in combination with a pharmaceutically acceptable carrier.

* * * * *